United States Patent [19]

Schlitt

[11] Patent Number: 4,959,551

[45] Date of Patent: Sep. 25, 1990

[54] COSMETIC TANNING LAMP AND SYSTEM HAVING ADJUSTABLE UVB PROPORTION

[75] Inventor: Steven C. Schlitt, Merrimac, Mass.

[73] Assignee: GTE Products Corporation, Danvers, Mass.

[21] Appl. No.: 315,647

[22] Filed: Feb. 27, 1989

[51] Int. Cl.$^5$ .......................... A61N 5/06; H01J 61/48
[52] U.S. Cl. ............................. 250/504 R; 250/494.1; 250/492.1; 313/487; 128/396
[58] Field of Search ............. 250/504 R, 494.1, 492.1; 313/487; 128/396

[56] References Cited

U.S. PATENT DOCUMENTS

| | | | |
|---|---|---|---|
| 3,466,443 | 9/1969 | Roesler et al. | 250/504 |
| 3,676,728 | 7/1972 | Schreurs | 313/487 |
| 4,645,969 | 2/1987 | Hoffman | 313/487 |
| 4,703,224 | 10/1987 | Rattray et al. | 313/487 |

*Primary Examiner*—Jack I. Berman
*Attorney, Agent, or Firm*—Carlo S. Bessone

[57] ABSTRACT

A fluorescent lamp and system for providing cosmetic tanning. The lamp includes a first ultraviolet-emitting phosphor disposed on a portion of the circumference of the interior of an ultraviolet-transmitting glass envelope. A second ultraviolet-emitting phosphor is disposed on the remaining portion the lamp envelope. The lamp further includes bases having electrical contacts extending therefrom and lying in a plane which passes through the demarcation lines formed between the first and second ultraviolet-emitting phosphors. In one embodiment, the proportions of UVB to UVA from the same light source are about 1.6 percent and 4.2 percent. In another aspect of the invention, a suntanning system includes an external reflector positioned adjacent the fluorescent lamp. The external reflector is effective in maintaining approximately the same irradiance level in the UVA region independent of the rotational alignment of the lamp.

3 Claims, 3 Drawing Sheets

COSMETIC TANNING LAMP AND SYSTEM HAVING ADJUSTABLE UVB PROPORTION

FIELD OF THE INVENTION

This invention relates in general to low pressure mercury vapor discharge lamps of the fluorescent type having a phosphor coating to emit skin tanning radiation when excited by the ultraviolet radiation generated from the mercury discharge.

BACKGROUND OF THE INVENTION

Skin pigmentation and thickening of the upper layer of the skin called the corneum are the body's natural protective reactions to exposure to shortwave ultraviolet energy produced by the sun; these reactions are the skin's defense against further assault.

Skin pigmentation, or tanning, is the result of a complex biological process, and to understand it, one most understand the skin's response to different wavelengths of ultraviolet radiation.

Deep down in the skin are special cells called melanocytes. Once these are stimulated with ultraviolet light, they will utilize substances which they have stored up to produce the pigment melanin. Because these substances only absorb shortwave (UVB) ultraviolet light, these UVB rays must be present in order to achieve melanin production. Longer wavelength ultraviolet (UVA) can also formulate melanin but only when there exists enough sensitizing material in the skin to bring about a UVB-type reaction. However, this requires a very high radiation UVA intensity for a long period of time. On the other hand, UVB can induce the same desired melanin production utilizing very low levels of radiation with more frequent exposures.

The pale pink colored melanin granules formed in the melanocytes will travel upward toward the horny layer or corneum. They are stored around the nuclei of the keratin cells there. In this manner, the pigment protects the UVB sensitive DNA located inside the nuclei without impeding the other positive effects of ultraviolet light.

In the preliminary stages of melanin production, very little protection is offered to the skin. In order to render the pigmentation process effective, the melanin granules must darken (oxidize). This requires a higher dosage of longer wave UVA.

The dosage of UVA must be sufficiently high in order to provide enough energy to initiate the oxidation process. It must be remembered that UVA rays are not as energetic as UVB rays. Longwave radiation is essential because high doses of shortware rays will activate substances in the body such as absorbic acid and cysteine which hinder the tanning process. These antioxidants not only inhibit oxidation of pigment but can even reverse the process.

Thus, UVB serves to synthesize the pigment granules while UVA ensure their oxidation. Together they form a light protection mechanism.

UVB is also essential in developing the skin callosity in the horny layer or corneum. This light-induced thickening stabilizes the skin to guarantee protection from excessive radiation. After the skin has been exposed several times, this callosity will develop within one to three weeks and can remain for several months.

Most tanning lamps produce a spectrum of ultraviolet light which is similar to that of the sun. Most lamps provide the small amount of UVB necessary to initiate the tanning process while at the same time, providing the UVA needed to darken the pigment (melanin).

Ultraviolet tanning lamps and tanning equipment used in the United States must comply with very specific regulations which are enforced by an agency of the Food and Drug Administration. These regulations restrict certain ultraviolet lamp characteristics and require extensive labeling of lamps and suntan equipment.

The U.S. FDA defines UVA as the region of 320 nanometers (nm) - 400 nm and UVB as the region of 260 nm-320 nm.

In the design of suntanning equipment and UV sources it is necessary to consider that tanning ability and tanning characteristics vary from one individual to another. In this regard there are two main factors which should be considered:

1. Skin Type—this refers to the (genetic) capability of an individual to produce and maintain a pigmentation in the skin. It is determined by the histologic response of the skin to ultraviolet radiation and classified by the observable effects.

2. Present Skin Pigmentation—this refers to the relative Pigmentation level of the skin at the time just prior to UV exposure. Previously well-tanned skin, exhibiting a high level of pigmentation is generally more resistant to erythema (sunburn) and hence may tolerate higher levels of UVB before the onset of Minimum Perceptible Erythema (MPE). Increased UVB will elicit, however, an increased melonogenic effect ultimately leading to a darker appearing skin. Previously, untanned skin will be more susceptible to UVB induced erythema and therefore UVB levels should be minimized in the early portion of an indoor tanning program.

Because of the factors mentioned above it is necessary in a commercial indoor tanning application or in the consumer tanning products marketplace to offer sunlamp products which are appropriate to the range of "tannable" skin types and skin conditions. This means that sunlamp product manufacturers, to be fully competitive, must offer products which produce the radiative characteristics necessary for safe and effective tanning of a range of skin types and conditions. To this end many manufacturers offer a variety of ultraviolet sources which when used in conjunction with their tanning equipment give the desired ranges of UVA and UVB appropriate for the person(s) undergoing the tanning process.

To cover the range of ultraviolet lamps to meet the needs of the market, equipment manufacturers and distributors generally make available three separate groups of lamps having the following characteristics: 1. Lamps with a relatively low proportion of UVB radiation approximately 1% UVB/UVA and lower, 2. Lamps with an intermediate proportion of UVB; approximately 1.0-3.0% UVB/UVA, and 3. Lamps with a relatively high proportion of UVB; 3% and above, usually to 5% maximum. In all cases, UVA is defined as the region of 320 nm-400 nm, UVB is defined as the region of 260 nm-320 nm.

In order to alter the UVB proportion of present tanning equipment one must actually replace lamps with others which have a different spectral characteristic. This necessitates the purchase and storage of an additional set of lamps. Another possibility is to alter the design of the tanning unit by installation or alteration of separate filters or reflectors. This latter option is even less desirable than the former in that the total output of the tanning unit will likely be reduced by such modifications. It is also inconvenient to maintain these materials and make the necessary installation.

SUMMARY OF THE INVENTION

It is, therefore, an object of the present invention to obviate the disadvantages of the prior art.

It is still another object of the invention to provide an improved suntanning fluorescent lamp to obviate the need for some of the separate classes of tanning lamp.

It is a further object of the invention to alter the UVB proportion of tanning equipment without the need to actually replace the exposure source (i.e., lamps) with a source having different spectral characteristics.

It is yet another object of the invention to provide an improved tanning system wherein approximately the same irradiance level in the UVA region is maintained independent of the rotational alignment of the lamp.

These objects are accomplished in one aspect of the invention by the provision of a suntanning fluorescent lamp comprising a glass envelope of substantially circular configuration in cross-section having axially opposed end portions. The envelope has an impurity level within a predetermined limit and is capable of transmitting UVA and UVB radiation. An electrode is located within each of the axially opposed end portions. An ionizable medium enclosed within the envelope includes an inert starting gas and a quantity of mercury. The ionizable medium when energized generates a plasma discharge comprising ultraviolet radiation and a limited proportion of visible radiation. A first ultraviolet-emitting phosphor means having a predetermined proportion of UVB to UVA radiation is disposed on a portion of the circumference of the interior surface of the envelope. A second ultraviolet-emitting phosphor means having a predetermined proportion of UVB to UVA is disposed on the remaining portion of the circumference of the interior surface of the envelope. The predetermined proportion of UVB to UVA of the second ultraviolet-emitting phosphor means is greater than the predetermined proportion of UVB to UVA radiation of the first ultraviolet-emitting phosphor means. The proportion of UVB to UVA of the combined emission from the first and second ultraviolet-emitting phosphor means is controllable by the rotational alignment of the fluorescent lamp.

In accordance with further teachings of the present invention, the predetermined proportion of UVB to UVA radiation of the first ultraviolet-emitting phosphor means is less than one percent. In a preferred embodiment, the first ultraviolet-emitting phosphor means comprises europium-activated strontium borate phosphor.

In accordance with further aspects of the present invention, the predetermined proportion of UVB to UVA radiation of the second ultraviolet-emitting phosphor means is within the range of from 10 percent to 12 percent. In a preferred embodiment, the second ultraviolet-emitting phosphor means comprises cerium-activated strontium magnesium aluminate phosphor.

In accordance with further aspects of the present invention, the proportion of UVB to UVA of the combined emission from the first and second ultraviolet-emitting phosphor means is about 1.6 percent and 4.2 percent, controllable by the rotational alignment of the fluorescent lamp.

In accordance with still further teachings of the present invention, the first ultraviolet-emitting phosphor is disposed on 180° of the circumference of the interior surface of the envelope. The second ultraviolet-emitting phosphor means is disposed on the remaining 180° portion of the circumference of the interior surface of the envelope. In a preferred embodiment, the lamp further includes a base associated with each of the end portions of the envelope and each base has pin means lies in a plane which passes through the demarcation lines formed between the first and second ultraviolet-emitting phosphor means.

These objects are accomplished in another aspect of the invention by the provision of a suntanning fluorescent lamp system which includes an external reflector means disposed adjacent the suntanning fluorescent lamp. The external reflector means is effective in maintaining approximately the same irradiance level in the UVA region independent of the rotational alignment of the suntanning fluorescent lamp.

BRIEF DESCRIPTION OF THE DRAWINGS

The invention will become more readily apparent from the following exemplary description in connection with the accompanying drawings, wherein.

BEST MODE FOR CARRYING OUT THE INVENTION

For a better understanding of the present invention, together with other and further objects, advantages and capabilities thereof, reference is made to the following disclosure and appended claims in connection with the above-described drawings.

Figure 1:
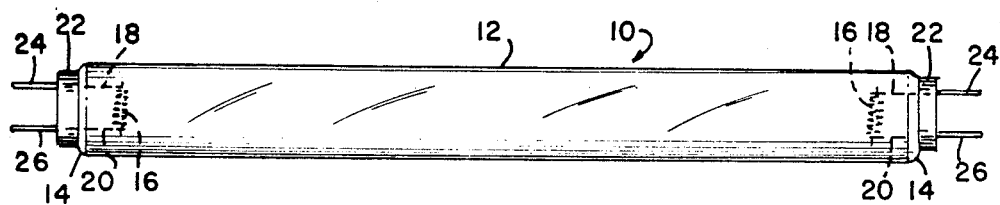
FIG. 1 represents a front elevational view of a suntanning fluorescent lamp according to the present invention.

Referring now to the drawings with greater Particularity, there is shown in FIG. 1 a lamp 10 including an envelope 12 of substantially circular configuration in cross-section having axially opposed end portions 14. Envelope 12 has a length between 30 cm and 200 cm and a diameter between 15 mm and 38 mm. Envelope 12 is capable of transmitting both UVA and UVB radiation. To produce the desired emission spectrum, the envelope should have a substantially low iron impurity level. Radiation within the region of 280 nanometers is absorbed by the envelope in proportion to the concentration of certain absorbing contaminants (e.g., iron oxide).

Preferably, the impurity level of iron oxide in envelope 12 is below about 0.055%. One suitable type of glass having the proper impurity levels and having the proper transmittance characteristic is available from GTE Products Corporation of Central Falls, R.I. as SG-81 glass. The UV transmittance characteristic of this glass is shown in Table 2 below:

TABLE 2

| TRANSMITTED WAVELENGTH (nm) | MAXIMUM % TRANSMISSION | MINIMUM % TRANSMISSION |
| --- | --- | --- |
| 270 | 1 | 0 |
| 280 | 3 | 1 |
| 290 | 11 | 8 |
| 300 | 31 | 27 |
| 310 | 54 | 50 |
| 320 | 75 | 67 |
| 330 | 85 | 77 |
| 340 | 90 | 82 |
| 350 | 91 | 83 |
| 360 | 91 | 85 |
| 370 | 91 | 87 |
| 380 | 91 | 89 |
| 390 | 91 | 90 |
| 400 | 91 | 91 |

An electrode 16 is located within each of the end portions 14 of envelope 12. Each electrode 16 comprises an alkaline earth oxide coated tungsten coil supported by lead-in wires 18 and 20. Envelope 12 encloses an ionizable medium including an inert starting gas and a quantity of mercury. The starting gas may consist of argon, neon, helium, krypton or a combination thereof at a low pressure in the range of about 1 to 4 mmHg. When energized, the ionizable medium generates a plasma discharge comprising ultraviolet radiation and a limited proportion of visible radiation. Suitable bases 22 are sealed to the ends of envelope 12 and may carry pin contacts 24 and 26.

Figure 2:
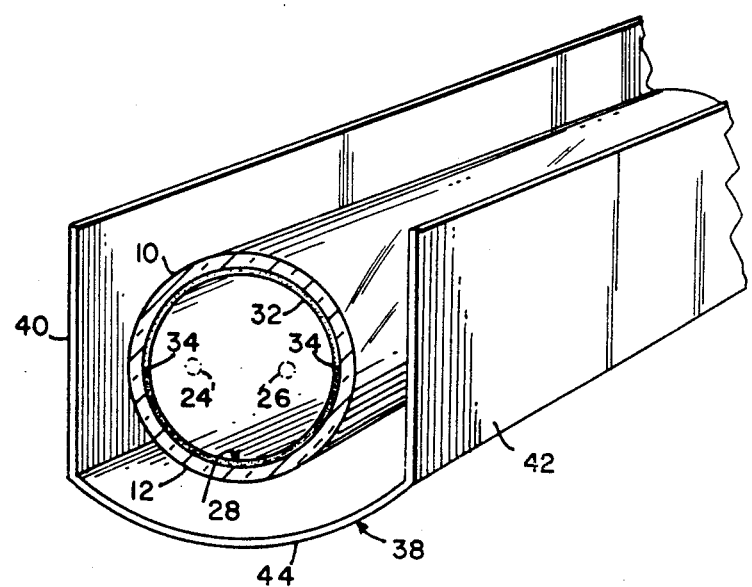
FIG. 2 is a perspective view, partially in cross-section illustrating the lamp of FIG. 1 with a reflector in accordance another aspect of the invention.

In the cross-section of lamp 10 shown in FIG. 2, a first ultraviolet-emitting phosphor 28 is disposed on the interior surface of envelope 12. First phosphor 28 is disposed on a 180° portion of the circumference of the interior surface of envelope 12 and extends the full length of envelope 12. One suitable phosphor is europium-activated strontium borate which is available from GTE Products Corporation, Towanda, Pa. as Sylvania Type 2051. This longwave ultraviolet-emitting phosphor exhibits peak emission at 370 nm with a half power bandwidth of approximately 20 nm. It exhibits a very low UVB spectral content. Typically, the proportion of UVB to UVA radiation from this phosphor is less than one percent.

A second ultraviolet-emitting phosphor 32 is disposed on the remaining 180° portion of the circumference of the interior surface of envelope 12 and also extends the full length of envelope 12. One suitable phosphor is cerium-activated strontium magnesium aluminate which is designated as Sylvania Type 2090. This phosphor has a peak emission at 340 nm with a half-power bandwidth of approximately 50 nm. The UVB emission content is relatively high for this phosphor type, with a typical range of 10%-12% UVB-/UVA. The proportion of UVB to UVA of the second ultraviolet-emitting phosphor 32 is greater than the proportion of UVB to UVA radiation of the first ultraviolet-emitting phosphor 28.

The following TABLE I shows the approximate phosphor powder weights for various lamp types.

TABLE I

| PHOSPHOR POWDER WEIGHTS | | | |
| --- | --- | --- | --- |
| | F20W/24" | F40W/48" | F100W/72" |
| Type 2090 | 0.70 g | 1.40 g | 2.10 g |
| Type 2051 | 0.75 g | 1.50 g | 2.24 g |
| Total Powder Weight | 1.45 g | 2.90 g | 4.34 g |

The application of the two phosphors can be accomplished by a prior art method known as roll coating. Such a coating operation may be automatically or manually performed. Following the application of the two phosphors, both coatings are allowed to dry in air and the bulb is then baked per the usual lehring operation known to the fluorescent lamp industry and further processed into a lamp using conventional means.

As best illustrated in FIG. 2, pins 24, 26 on each of the lamp bases 22 lie in a plane which passes through the demarcation lines 34 formed between the first and second ultraviolet-emitting phosphors 28, 32. The proportion of UVB to UVA of the combined emission from first and second ultraviolet-emitting phosphors 28, 32 is controllable by the rotational alignment of the fluorescent lamp within its fixture. With the bipin bases 22, the lamp can be rotated into one of two different positions.

The lamp bases may vary from the bipin bases 22 depicted in FIG. 1. For example, the lamp may be provided with a single pin base at each end. By rotating the lamp within the 360 degree range, the UVB to UVA proportion is continuously variable.

In accordance with further aspects of the invention, an external reflector 38 is disposed adjacent lamp 10 as illustrated in FIG. 2. Reflector 38 blends the spectrum of the backward irradiance with the spectrum of the forward irradiance and on the whole maximizes the total UV irradiance. Moreover, the reflector of the present invention is effective in maintaining approximately the same irradiance level in the UVA region independent of the rotational alignment of lamp 10.

The general positioning and construction of reflector 38 is shown in the cross-sectional view of FIG. 2. Reflector 38 resembles a trough having parallel planar sidewalls 40, 42 which extend the length of the envelope. Sidewalls 40, 42 vertically extend to a flush position with respect to the top surface lamp 10. A bottom portion 44 of reflector 38 is located below lamp 10 and joins sidewalls 40, 42 and runs horizontally to a normal reference plane. Preferably, lamp 10 is located equidistant from sidewalls 40, 42 and bottom portion 44. One suitable material for forming reflector 38 is an aluminum product called Alzak which is a registered trademark of Alcoa Aluminum Company.

It was discovered that the configuration as illustrated in FIG. 2 is effective in maintaining approximately the same irradiance level in the UVA region independent of the rotational alignment of the suntanning lamp. It is understood that the particular material, shape and positioning of the reflector may differ from that described without departing from the scope of the invention.

Figure 3:
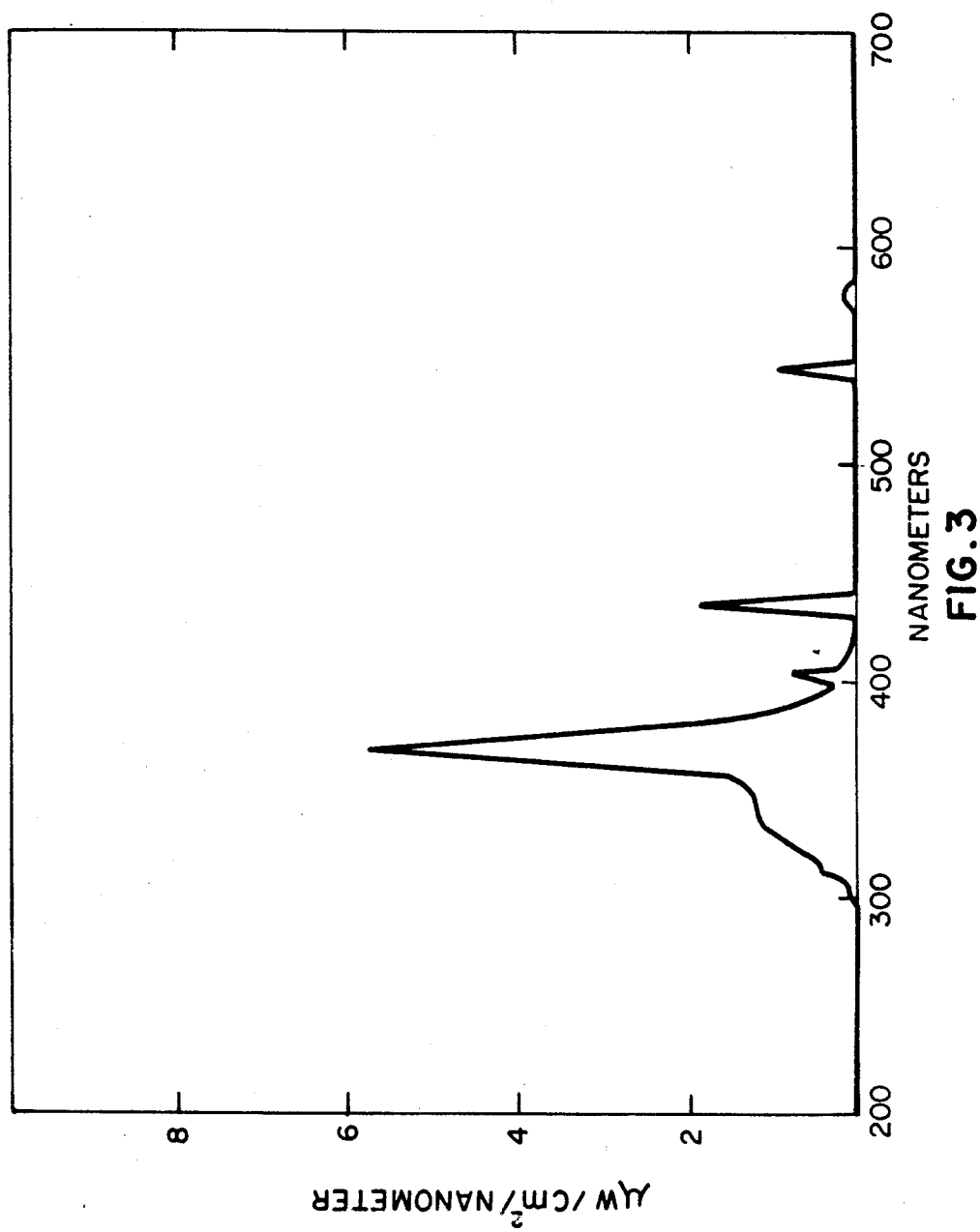
FIG. 3 is a graph depicting one combined spectral energy distribution from the lamp and reflector of FIG. 2.

When the lamp is mounted such that the phosphor coating 32 is in the top position and coating 28 is in the downward position the combined emission spectrum as illustrated in FIG. 3 is produced. With the lamp in this position the resulting UVA and UVB proportions are such that a ratio of 4.2% of UVB/UVA is realized, with UVA equal to 1559.8$\mu$W/cm$^2$ and a measured UVB level of 64.96$\mu$W/cm$^2$. Using the erythemal sensitivity response curve as established by German DIN 5031, (corresponding to that proposed by the CIE), which is widely accepted, a weighted UVB level of 4.43$\mu$W/cm$^2$ of effective erythemal irradiance was calculated for the lamp mounted in this position.

The center for Devices and Radiological Health (CDRH), an agency of the FDA which regulates the use of tanning products in the U.S., has published a value of 156J/M$^2$ at 296 nm as equivalent to one Minimum Erythemal Dose (MED) for untanned Type II skin. The formula then for determining the time exposure (Te) for one MED is:

$$Te(\text{sec}) = \frac{156 J/M^2}{\Sigma V_i R_i}$$

where
$V_i$ = weighting factors per DIN 5031 1
$R_i$ = irradiance in W/M² and
$\Sigma V_i R_i$ = weighted UVB irradiance from 250–315 nanometers.

By calculation, then it is obvious that in the above-mentioned positioning of the lamp a time exposure of approximately 3521 seconds (or 58.7 minutes) will produce one MED.

Figure 4:
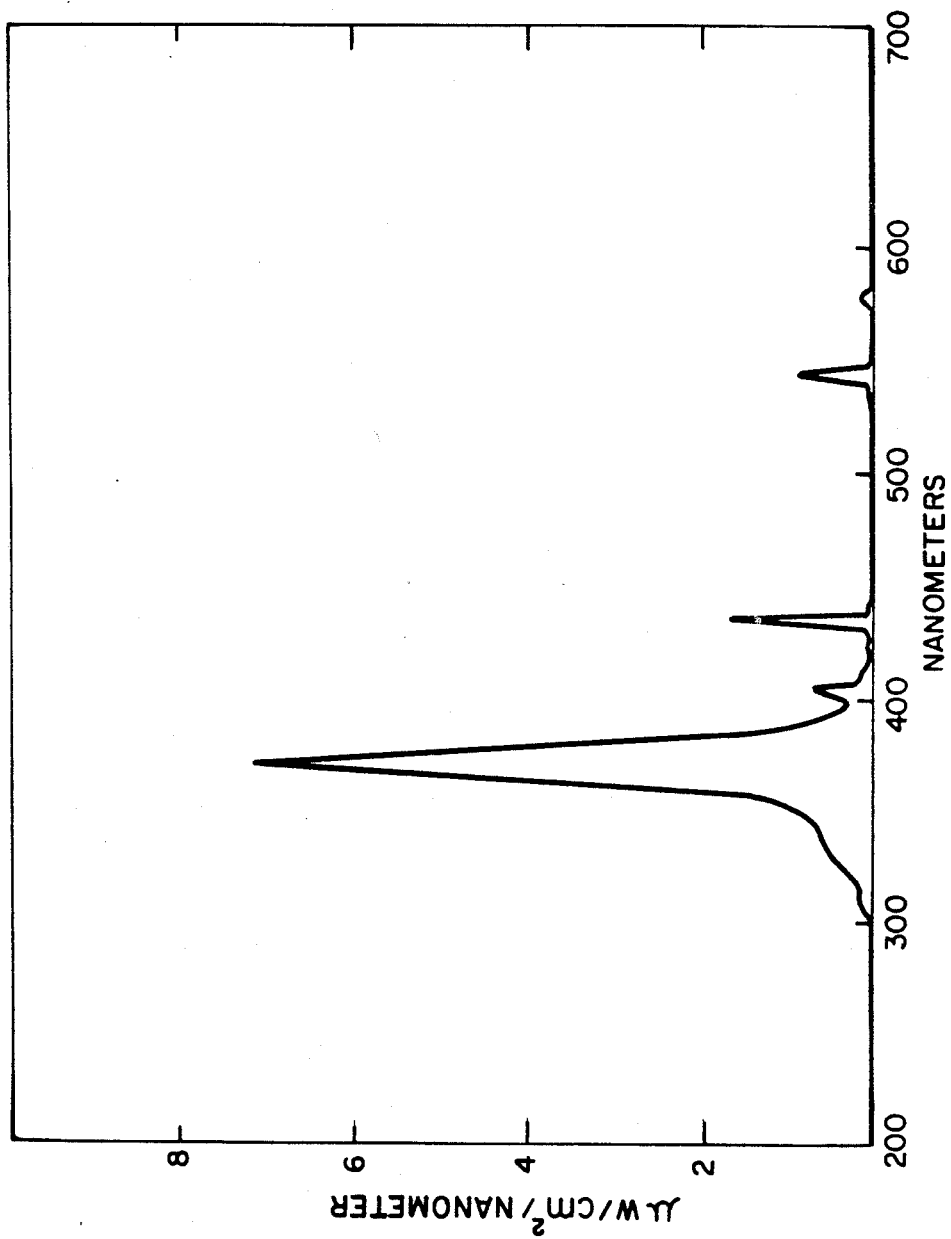
FIG. 4 is a graph depicting another combined spectral energy distribution produced by rotating the lamp of FIG. 2 by 180°.

To illustrate the versatility of the invention and to further support its primary objective, the lamp may be mounted into standard lampholders such that the phosphor coating 32 is now in the downward position and the coating 28 is in the upward position facing the person to be irradiated. With this configuration it is shown by the data that a ratio of UVB/UVA of only 1.6% is produced. A UVA level of 1610µW/cm² and a UVB level of only 25.3µW/cm² is realized with the lamp so positioned. FIG. 4 is representative of irradiance on the subject's skin when the lamp is positioned as aforementioned. Using the erythemal sensitivity response curve as previously mentioned an effective erythemal irradiance of 1.67µW/cm² was calculated.

Under the above-mentioned conditions a time exposure of 9341 seconds, or 156 minutes would be required to produce a Minimum Erythemal Dose. This is approximately 2.65 times the time required for lamp as positioned in the reverse orientation.

There has thus been shown and described a fluorescent lamp and system for use in cosmetic tanning. The proportion of UVB to UVA radiation of the combined spectral emission from the first and second ultraviolet-emitting phosphors is adjustable by rotating the lamp within its electrical socket. Moreover, approximately the same irradiance level in the UVA region is maintained independent of the rotational alignment and the UVB to UVA proportions produced by the lamp. The teachings of the invention can be built into new equipment designs or, in part, retrofitted to existing equipment. The need for maintaining an inventory and the replacement of separate classes of tanning lamps is eliminated by replacement with a single lamp type.

While there have been shown and described what are at present considered to be the preferred embodiments of the invention, it will be apparent to those skilled in the art that various changes and modifications can be made herein without departing from the scope of the invention. The basic configuration of the phosphors with respect to each other need not be precisely as described herein. It is possible that coatings of 240°/120° or other combination may produce similar results to those described here.

What is claimed is:

1. A suntanning system comprising:
    a fluorescent lamp including an ultraviolet-transmitting glass envelope of substantially circular configuration in cross-section, a first ultraviolet-emitting phosphor means having a predetermined proportion of UVB to UVA radiation disposed on a portion of the circumference of the interior surface of said envelope, a second ultraviolet-emitting phosphor means having a predetermined proportion of UVB to UVA disposed on the remaining portion of said circumference of said interior surface of said envelope, said predetermined proportion of UVB to UVA of said second ultraviolet-emitting phosphor means being greater than said predetermined proportion of UVB to UVA radiation of said first ultraviolet-emitting phosphor means, the proportion of UVB to UVA of the combined emission from said first and second ultraviolet-emitting phosphor means being controllable by the rotational alignment of said fluorescent lamp; and
    an external reflector means disposed adjacent said fluorescent lamp, said external reflector means being effective in maintaining the irradiance level in the UVA region at approximately the same level independent of the rotational alignment of said fluorescent lamp.

2. The suntanning system as set forth in claim 1 wherein said reflector means is trough-shaped having parallel sidewalls and a portion joining said sidewalls.

3. The suntanning system as set forth in claim 2 where said reflector means extends the length of said lamp and is positioned equidistant from said sidewalls and said joining portion.

* * * * *